United States Patent
Xu

(10) Patent No.: US 10,400,009 B2
(45) Date of Patent: Sep. 3, 2019

(54) β-SHEET BREAKER PEPTIDE USED FOR PREVENTING AND/OR TREATING ALZHEIMER'S DISEASE

(71) Applicant: TIANJIN MEDICAL UNIVERSITY, Tianjin (CN)

(72) Inventor: Shumei Xu, Tianjin (CN)

(73) Assignee: Tianjin Medical University, Tianjin (CN)

( * ) Notice: Subject to any disclaimer, the term of this patent is extended or adjusted under 35 U.S.C. 154(b) by 0 days.

(21) Appl. No.: 15/508,652

(22) PCT Filed: Sep. 4, 2014

(86) PCT No.: PCT/CN2014/085921
§ 371 (c)(1),
(2) Date: Mar. 3, 2017

(87) PCT Pub. No.: WO2016/033774
PCT Pub. Date: Mar. 10, 2016

(65) Prior Publication Data
US 2017/0305969 A1    Oct. 26, 2017

(51) Int. Cl.
| | |
|---|---|
| A01N 37/18 | (2006.01) |
| A61K 38/00 | (2006.01) |
| A61K 38/04 | (2006.01) |
| A61K 35/30 | (2015.01) |
| A61K 31/00 | (2006.01) |
| C07K 7/06 | (2006.01) |
| C07K 14/47 | (2006.01) |

(52) U.S. Cl.
CPC ............ *C07K 7/06* (2013.01); *C07K 14/4711* (2013.01); *A61K 38/00* (2013.01)

(58) Field of Classification Search
None
See application file for complete search history.

(56) References Cited

FOREIGN PATENT DOCUMENTS

| | | |
|---|---|---|
| CN | 101531703 | 9/2009 |
| CN | 102058887 | 5/2011 |
| CN | 102260349 | 11/2011 |
| CN | 102516357 | 6/2012 |
| CN | 104277092 | 1/2015 |
| WO | 2009/007934 | 1/2009 |

OTHER PUBLICATIONS

International Search Report and Written Opinion, Corresponding to International Application No. PCT/CN2014/085921, dated May 29, 2015.
International Preliminary Report on Patentability, Chapter I, Corresponding to International Application No. PCT/CN2014/085921, dated Mar. 7, 2017.
Atul Deshpande et al., Different Conformations of Amyloid β Induce Neurotoxicity by Distinct Mechanisms in Human Cortical Neurons. The Journal of Neuroscience, 2006, 26(22): 6011-6018.
M. Q. Liao et al., The correlation between neurotoxicity, aggregative ability and secondary structure studied by sequence truncated Aβ peptides. FEBS Letters, 581 (2007) 1161-1165.
Tarek Mohamed et al., Amyloid cascade in Alzheimer's disease Recent advances in medicinal chemistry. European Journal of Medicinal Chemistry, 113 (2016) 258-272.
Robert Ehehalt et al., Amyloidogenic processing of the Alzheimer β-amyloid precursor protein depends on lipid rafts. The Journal of Cell Biology, vol. 160, No. 1, 2003 113-123.
Matthew L. Hemming et al., Amyloid β-Protein Is Degraded by Cellular Angiotensin converting Enzyme (ACE) and Elevated by an ACE Inhibitor. J Biol Chem 2005, 280(45) 37644-37650.
Elizabeth A. Eckman., Degradation of the Alzheimer's Amyloid β Peptide by Endothelin converting Enzyme. The Journal of Biological Chemistry. vol. 276, No. 27, 2001, pp. 24540-24548.
Miia Kivipelto et al., Midlife vascular risk factors and Alzheimer's disease in later life longitudinal, population based study. BMJ 2001; 322: 1447-51.
Wesley Farris et al., Partial Loss-of-Function Mutations in Insulin-Degrading Enzyme that Induce Diabetes also Impair Degradation of Amyloid β-Protein. American Journal of Pathology, vol. 164, No. 4, 2004: 1425-1434.
G Scott Ralph et al., Silencing mutant SOD1 using RNAi protects against neurodegeneration and extends survival in an ALS model. Nature Medicine, vol. 11, No. 4, 2005: 429-433.
Ming Jin et al., Soluble amyloid β-protein dimers isolated from Alzheimer cortex directly induce Tau hyperphosphorylation and neuritic degeneration. PNAS, vol. 108, No. 14, 2011: 5819-5824.
John Hardy et al., The Amyloid Hypothesis of Alzheimer's Disease Progress and Problems on the Road to Therapeutics. Science, 297(5580), 2002: 353-356.
Claudio Soto et al., The conformation of Alzheimer's β peptide determines the rate of amyloid formation and its resistance to proteolysis. Biochem. J. (1996) 314, 701-707.
H. Michael Tucker et al., The Plasmin System Is Induced by and Degrades Amyloid-β Aggregates. The Journal of Neuroscience, 2000, 20(11): 3937-3946.

*Primary Examiner* — Olga N Chernyshev
(74) *Attorney, Agent, or Firm* — Leydig, Voit & Mayer, Ltd.

(57) ABSTRACT

Provided in the present invention are a β-sheet breaker peptide used for preventing and/or treating Alzheimer's disease, and the use thereof for preventing and/or treating Alzheimer's disease. The amino acid sequence of the β-sheet breaker peptide is His-Lys-Gln-Leu-Pro-Phe-Tyr-Glu-Glu-Asp (SEQ ID NO:1). The polypeptide can specially bind to a β-amyloid protein monomer ($A\beta_{1-42}$), and prevent the formation of β-sheet, thereby inhibiting Aβ peptide aggregation, reducing the formation of Aβ soluble oligomer, Aβ fiber and senile plaques in the brain, and accelerating the degradation and removal of Aβ peptide.

6 Claims, 7 Drawing Sheets
Specification includes a Sequence Listing.

Product Name:HD-10
Instrument No: 0200023
Lot No    :P120711-XP274055
Analyst   :ZJM
Column    :4.6*250mm,Venusil XBP C18(L)
Solvent A :0.1%Trifluoroacetic  in 100% Acetonirile
Solvent B :0.1%Trifluoroacetic  in 100% Water
Gradient  :           A         B
            0.01min   15%       85%
            25min     40%       60%
25.1min   100%        0%
            30min         Stop
Flow rate :1.0ml/min
Wavelength :220nm
Volume: 10ul

| Rank | Time   | Conc.  | Area    | Height |
|------|--------|--------|---------|--------|
| 1    | 10.755 | 0.5482 | 34691   | 3035   |
| 2    | 12.093 | 0.7807 | 49401   | 1489   |
| 3    | 13.618 | 1.064  | 67298   | 37473  |
| 4    | 13.763 | 96.86  | 6128842 | 376373 |
| 5    | 14.192 | 0.7535 | 47681   | 4419   |
| Total |       | 100    | 6327913 | 422789 |

β-SHEET BREAKER PEPTIDE USED FOR PREVENTING AND/OR TREATING ALZHEIMER'S DISEASE

CROSS-REFERENCE TO RELATED APPLICATIONS

This application is a U.S. National Stage Application filed under 35 U.S.C. § 371 of International Application No. PCT/CN2014/085921, filed Sep. 4, 2014, hereby incorporated by reference in its entirety.

TECHNICAL FIELD

The present invention relates to polypeptides and use thereof. In particular, the present invention relates to a class of β-sheet blocking peptide which can be used for prevention and/or treatment of Alzheimer's disease, and the use thereof in prevention and/or treatment of Alzheimer's disease.

BACKGROUND ART

Alzheimer's disease (AD), also named senile dementia, is a type of neurodegenerative disease. With the acceleration of population aging process, senile diseases have become outstanding problems affecting human health. Senile dementia, malignant tumors and cardio-cerebrovascular accident are three leading diseases which cause the death of the elderly. World Health Organization has listed AD as one of the five major diseases in the 21st Century.

Modern medicine has proved that the major pathological changes of AD have the following features: a great number of senile plaques (SP) formed among nerve cells due to the deposition of β-amyloid peptide (Aβ); neurofibrillary tangle (NT) in nerve cells; and extensive neuron loss. Currently, the theory of β-amyloid protein is predominant in the understanding of AD pathogenesis. In this theory, it is believed that the pathological fold of Aβ and the formation of oligomer initiate the onset process of AD, such as the formation of oxygen free radical, oxidative stress, the destruction of intracellular calcium ion homeostasis, the activation of protein kinases, the hyperphosphorylation of tau protein, the induction of apoptosis, chronical inflammation, complement activation, and the influence on mitochondrial function, which lead to pathophysiological changes such as energy metabolism disorders and finally the death of nerve cells, thereby causing a series of clinical symptoms in AD patients, such as memory loss, the decline of cognitive performance, and abnormal behaviors.

A lot of evidences indicate that the neurotoxic effect of Aβ is the common pathway of AD pathogenesis caused by various factors, and the neurotoxicity of Aβ is associated with its aggregation. In the secondary structure of Aβ, the formation of β-sheet is essential for Aβ aggregation, while β-sheet abundant structures can promote Aβ aggregation more quickly. The formation of β-sheet is associated with the hydrophobic fragments in Aβ peptide chains. Under certain conditions, the exposure of hydrophobic regions in β-sheet abundant structures will promote Aβ aggregation, oligomer formation, and eventually the formation of insoluble materials deposited in the intercellular space of neurons. This may result in neurotoxicity and the increased activities of glial cells in the brain, producing inflammatory mediators and complements which may together form amyloid plaques. Research found that the level of soluble Aβ ingredient has a closer relationship with the severity of cognitive impairment than the density of plaque deposition. Different Aβ soluble oligomers, such as Aβ oligomer, ADDLS and Aβ fiber, may affect neurological functions and neurological viability by different neurotoxic mechanisms (Deshpande A, Mina E, Glabe C. Different Conformations of Aβ Induce Neurotoxicity by Distinct Mechanisms in Human Cortical Neurons[J]. J Neurosci, 2006, 26(22):6011-6018).

As the main ingredient of senile plaques, Aβ is a metabolite of the hydrolysis of amyloid precursor protein (APP) by β- or γ-secretase. Whether $A\beta_{1-40}$ or $A\beta_{1-42}$ is produced depending on the enzymatic cleavage sites. Compared with $A\beta_{1-40}$, $A\beta_{1-42}$ has higher neurotoxicity and hydrophobicity, is more prone to form oligomers and further aggregate, and thus plays a key role in AD pathological process.

The primary structure of $A\beta_{1-42}$ peptide is shown as follows (SEQ ID NO: 3):

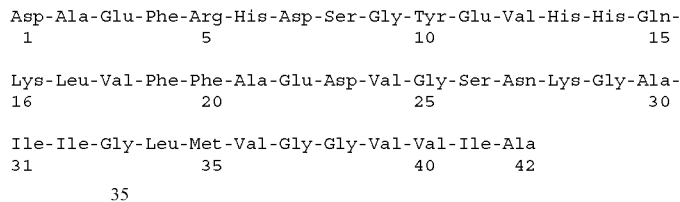

The ten amino acid residues 33-42 at C-terminal and amino acid residues 17-21 of $A\beta_{1-42}$ are highly hydrophobic and constitute the hydrophobic regions of $A\beta_{1-42}$. Amino acid residues 28-42 are more likely to form a β-sheet conformation, and amino acid residues 9-21 may also form a β-sheet conformation. β-sheet conformation is favorable to $A\beta_{1-42}$ peptide aggregation, which results from the interaction between its hydrophobic regions. Using spectroscope and cellular technologies, M Q Liao et al. find the hydrophobic fragments of amino acid residues 17-21 and 25-35, and amino acid residues 41-42 at C-terminal of $A\beta_{1-42}$ peptide chain are the main regions which cause aggregation and neurotoxicity (Liao M Q, Tzeng Y J, Chang L Y, et al. The correlation between neurotoxicity, aggregative ability and secondary structure studied by sequence truncated Abeta peptides[J]. FEBS Lett, 2007, 581(6):1161-1165).

The object of recent studies on the drugs against Aβ is reducing Aβ formation, increasing Aβ clearance, preventing or reversing Aβ aggregation, and inhibiting Aβ toxicity, and so on. Researchers from the Medicine School of Washing University (US) surprisingly found that the brain cells of AD mice start to restore functions after the amyloid protein plaques in their brains are removed, which indicates a promising prospect of the drugs against Aβ. Among various drugs against Aβ, β-sheet blocking agents draw increasing attention of researchers.

Chinese patent CN 101531703A discloses a few of polypeptides which can specially bind to $A\beta_{1-42}$, stabilize its normal spatial structure, inhibit the formation of β-sheet, prevent the formation of soluble β-amyloid protein oligomers and β-amyloid protein plaques, and degrade Aβ fibers.

These polypeptides are named β-sheet blocking peptides. After comparison, it is found that the polypeptide having the sequence of His-Lys-Gln-Leu-Pro-Phe-Phe-Glu-Glu-Asp (H102) (SEQ ID NO:2) has the strongest inhibition on Aβ aggregation (inhibitory rate: 27.84%).

In the art, there are still requirements for new active drugs which are designed to better target at the essential β-sheet in Aβ aggregation. Said drugs can specially bind to β-amyloid protein monomer ($AB_{1-42}$), prevent the formation of β-sheet and further inhibit Aβ peptide aggregation, reduce the formation of Aβ soluble oligomer, Aβ fiber and senile plaques in the brain, accelerate the degradation and removal of Aβ peptide, and accordingly can be used for prevention and/or treatment of AD.

SUMMARY OF THE INVENTION

One object of the present invention is to provide a polypeptide which is designed to better target at the essential β-sheet in Aβ aggregation. Said polypeptide can specially bind to β-amyloid protein monomer ($A\beta_{1-42}$), prevent β-sheet formation and further inhibit Aβ peptide aggregation, reduce the formation of Aβ soluble oligomer, Aβ fiber and senile plaques in the brain, accelerate the degradation and removal of Aβ peptide, and accordingly can be used for prevention and/or treatment of AD.

The inventor surprisingly found that the polypeptide HPYD having the following amino acid sequence could achieve the above-mentioned object:

```
                                      (SEQ ID NO: 1)
    His-Lys-Gln-Leu-Pro-Phe-Tyr-Glu-Glu-Asp.
```

Therefore, in the first aspect of the invention, provided is a polypeptide comprising the above-mentioned amino acid sequence.

Since the above-mentioned polypeptide can specially bind to β-amyloid protein monomer ($A\beta_{1-42}$), stabilize its normal spatial structure, inhibit the formation of β-sheet, prevent the formation of soluble β-amyloid protein oligomers and β-amyloid protein plaques, and degrade Aβ fibers, they can be used for prevention and/or treatment of AD.

Therefore, in the second aspect of the invention, provided is use of the polypeptide of the invention in the manufacture of a medicament for prevention and/or treatment of AD.

In the third aspect of the invention, provided is a pharmaceutical composition comprising the polypeptide of the invention and a pharmaceutically acceptable carrier.

In the fourth aspect of the invention, provided is a method for prevention and/or treatment of AD in a subject, comprising administering an effective amount of the polypeptide of the invention to the subject.

DESCRIPTION OF THE FIGURES

FIG. 1 shows the steps of a method for preparing the polypeptide of the invention and the detection results of the prepared products.

FIG. 3A shows the electron microscopy result of incubation of $A\beta_{1-42}$ alone for 5 days, magnification=57000×; FIG. 3B shows the electron microscopy result of co-incubation of H102 and $A\beta_{1-42}$ for 5 days, magnification=57000×; FIG. 3C shows the electron microscopy result of co-incubation of HPYD and $A\beta_{1-42}$ for 5 days, magnification=57000×.

DETAILED DESCRIPTION OF THE INVENTION

Figure 1A:
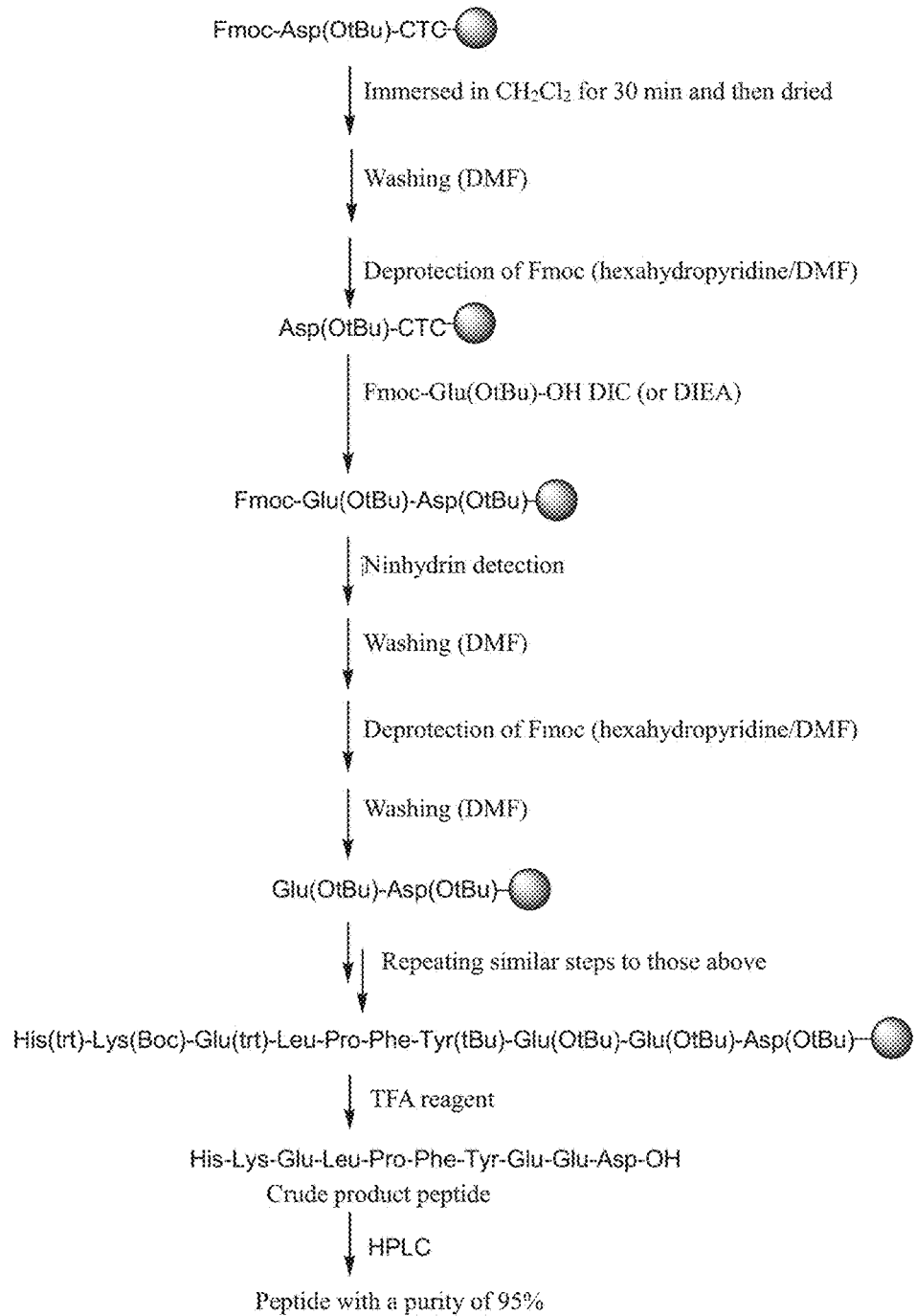
FIG. 1A shows the main steps for synthesizing and purifying the polypeptide HPYD of the invention.

Disclosed herein are amino acid sequences of a series of polypeptides. Those skilled in the art could understand that the sequence in which an amino acid residue is shown in three-letter form indicates the sequence of a polypeptide from its N-terminal (amino-terminal) to its C-terminal (carboxy-terminal). For example, when the sequence of a polypeptide is indicated as "His-Lys-Gln-Leu-Pro-Phe-Tyr-Glu-Glu-Asp" (SEQ ID NO:1), it means the sequence of this polypeptide is "N-terminal-His-Lys-Gln-Leu-Pro-Phe-Tyr-Glu-Glu-Asp-C-terminal".

In the first aspect of the invention, a polypeptide comprising the following amino acid sequence is provided:

```
                                      (SEQ ID NO: 1)
    His-Lys-Gln-Leu-Pro-Phe-Tyr-Glu-Glu-Asp.
```

The polypeptide of the invention may comprise, substantially consist of, or consist of the above-mentioned amino acid sequence.

In one embodiment of the invention, provided is a polypeptide consisting of the following sequence, which is designated as HPYD in the invention:

HPYD:

(SEQ ID NO: 1)
His-Lys-Gln-Leu-Pro-Phe-Tyr-Glu-Glu-Asp.

It is apparent that various modifications can be made to the polypeptide of the invention. Said modifications include but are not limited to: hydroxylation of proline and lysine, methylation of o-amino group on the side chain of lysine or histidine, acetylation of N-terminal amino, and, in some cases, amidation of C-terminal carboxyl. It should be understood that, it is apparent for those skilled in the art to make the above various modifications based on the amino acid sequence of the polypeptide of the invention, and these modified polypeptides which comprises the disclosed amino acid sequences are also encompassed within the scope of the present invention.

The above-mentioned polypeptides of the present invention can be used as β-sheet blocking peptide, which can specifically bind to β-amyloid protein monomer ($A\beta_{1-42}$), stabilize its normal spatial structure, inhibit the formation of β-sheet, prevent the formation of soluble β-amyloid protein oligomers and β-amyloid protein plaques, degrade Aβ fibers, and thus can be used as medicaments for prevention and/or treatment of Alzheimer's disease.

Therefore, in another aspect of the invention, provided is use of the polypeptide of the invention in the manufacture of a medicament for prevention and/or treatment of Alzheimer's disease.

The term "prevent", "preventing" or "prevention" as used herein refers to reducing the risk of a subject suffering from the disease, or delaying the time point of the onset of a disease or its symptoms. The term "treat", "treating" or "treatment" as used herein may not necessarily refer to complete cure, but may refer to ameliorating the symptoms of a potential disease and/or reducing one or more potential cellular, physiological or biochemical causes or mechanisms which could lead to the symptoms. It should be appreciated that "ameliorating" as used herein is relative to the conditions of a disease, and includes not only the physiological conditions, but also the molecular conditions of the disease.

The present invention also provides a pharmaceutical composition comprising one or more polypeptides of the invention and a pharmaceutically acceptable carrier.

The term "pharmaceutically acceptable carrier" as used herein refers to a substance which will not cause any adverse effect in terms of biology or other respects. That is to say, the substance can be administered to a subject together with the polypeptide of the invention without causing any adverse biological effect or interacting with any other component in the pharmaceutical composition in an undesirable manner. It is evident and well known to those skilled in the art that the carrier should be selected to minimize any degradation of the active ingredients and any adverse side effect in the subject.

The pharmaceutical composition of the invention generally comprises at least one polypeptide of the invention and one or more pharmaceutically acceptable carriers. Suitable carriers include but not limited to: antioxidants, preservatives, colorants, flavoring agents and diluents, emulsifiers, suspending agents, solvents, filters, bulking agents, buffering agents, vehicles, thinner, excipients and/or pharmaceutical adjuvants. For example, a suitable carrier can be normal saline solution, citrate buffer or artificial CSF, and other substances which may be added to a conventional parenteral composition. Neutral buffered saline or saline mixed with serum albumin are also exemplary carriers. Those skilled in the art could easily determine various buffering agents which can be used in the composition and dosage form of the invention. Typical buffering agents include, but are not limited to, pharmaceutically acceptable weak acids, weak bases or combinations thereof. Preferably, the buffering components are water-soluble substances, such as phosphoric acid, tartaric acid, lactic acid, succinic acid, citric acid, acetic acid, ascorbic acid, aspartic acid, glutamic acid, and the salts thereof.

The primary solvents in the carriers can be aqueous or non-aqueous in nature. Furthermore, the carriers can include other pharmaceutically acceptable excipients which can be used to improve or maintain the pH, permeability, viscosity, clarity, color, sterility, stability, dissolution rate or odor of the formulation. The pharmaceutical composition of the invention can also include other pharmaceutical acceptable carriers which can be used to improve or maintain the release rate of the polypeptide of the invention. Such carriers are known to the person skilled at preparing sustained release formulations.

When the pharmaceutical compositions of the invention have been formulated, they can be stored in sterile tubes in the forms of solution, suspension, gel, emulsion, solid, dehydrated or lyophilized powder. These formulations can also be stored in ready-to-use form, in lyophilized powder form needed to be reconstituted before use, or in liquid form needed to be diluted before use. Preferably, the pharmaceutical compositions of the invention are provided in the form of sterile tubes for a single use, and stored at 2-8° C. before use Immediately before administration, the pharmaceutical composition of the invention can be appropriately diluted with any suitable sterile buffer as described above, such as citrate buffer.

The present invention also provides a method for prevention and/or treatment of Alzheimer's disease in a subject, comprising administering an effective amount of the polypeptide of the invention to the subject.

The term "effective amount" as used herein means the amount of the compound used which is sufficient to prevent the onset of a disease or its symptoms, or to ameliorate one or more causes or symptoms of the disease or condition. The amelioration may be alleviating or improving but not necessarily eliminating. For the polypeptide of the invention, its effective amount for prevention and/or treatment should be varied depending on the targeted individual and the polypeptide used. The effective amount of the polypeptide used for prevention and/or treatment should also be varied depending on many factors, such as age, shape, weight, and conditions of the individual. For a particular subject, determination of the prevention and/or treatment effective amount of the polypeptide of the invention is within the ability of those skilled in the art.

When the polypeptides or the prevention and/or treatment methods of the invention are applied to Alzheimer's disease subjects, they will have significant effects of inhibiting Aβ aggregation in the brain tissues of the subjects, reducing the quantity and area of amyloid plaques, and improving the symptoms of Alzheimer's disease. For example, they can be used to improve activity and attention and reduce response time, to improve pronunciation, facial expression, posture, smell, sexuality, sexual function and emotional status, and to induce a happy mental state. In another embodiment of the present invention, the polypeptide of the invention can be appropriately administered to Alzheimer's disease patients as a cognitive enhancing agent, thereby increasing learning abilities, especially those damaged by dementia, or inhibiting cognitive decline and/or dementia.

Preparation of the Polypeptide of the Invention

The polypeptide of the invention can be prepared by any method for preparing polypeptides known to those skilled in the art.

The polypeptide of the invention can be synthesized by chemical synthesis. The synthesis of a polypeptide can be carried out in solution or by solid-phase synthesis. Solid-phase synthesis methods of a polypeptide include Fmoc solid-phase synthesis and tBoc solid-phase synthesis. The artificial synthesis methods of a polypeptide are generally carried out from the C-terminal (carboxyl-terminal) to the N-terminal (amino-terminal) of the polypeptide.

In one embodiment of the present invention, the polypeptide of the invention is synthesized by Fmoc solid-phase synthesis and purified by HPLC. FIG. 1 shows the main steps of synthesizing and purifying the polypeptide HPYD of the invention in this embodiment, and the test results of the prepared polypeptide. In this embodiment, the polypeptide is synthesized on a synthesis column using a solid-phase polypeptide synthesizer, such that the difficulty of product purification can be greatly reduced. In order to prevent side reactions, the synthesis column and the side chains of the added amino acids are protected. The C-terminal is free and must be activated before the reaction. After the polypeptide of the invention is synthesized by Fmoc synthesis and purified by preparative high performance liquid chromatography (HPLC) column, they can be identified by mass spectrometry (MS) analysis. It should be appreciated that all the polypeptides of the invention can be prepared, purified and identified by similar methods to those as described in the above embodiments.

The polypeptide of the invention can also be produced by recombinant genetic engineering. Briefly, a polynucleotide encoding a polypeptide of the invention can be synthesized and then transformed into a suitable host cell using the known methods in the art. Then the transformed polynucleotide can be expressed in the host cell. The expressed product can be purified or processed to obtain the polypeptide of the invention.

EXAMPLES

The present invention is further illustrated in view of the following examples, with which those skilled in the art may obtain better understanding of the invention. These examples are provided only for exemplary purpose rather than intending to limit the scope of the invention. Efforts have been made to ensure the accuracy of related numbers (such as quantity and temperature). Nevertheless, it should be considered that some errors and deviations may exist. Unless otherwise indicated, the parts are parts by weight, the temperature is expressed in ° C. or as ambient temperature, the pressure is close to or equal to atmospheric pressure.

Example 1. Preparation of HPYD

In this example, the polypeptide HPYD of the invention was synthesized using Fmoc/tBu solid-phase synthesis. The sequence of said polypeptide is shown as follows:

(SEQ ID NO: 1)
His-Lys-Gln-Leu-Pro-Phe-Tyr-Glu-Glu-Asp

In the synthesis method of the polypeptide in this example, the following starting materials were used: Fmoc-Asp(OtBu)-CTC Resin, Fmoc-Glu(OtBu)-OH, Fmoc-Tyr(tBu)-OH, Fmoc-Phe-OH, Fmoc-Pro-OH, Fmoc-Leu-OH, Fmoc-Gln(trt)-OH and Fmoc-Lys(Boc)-OH.

The main steps of the methods for synthesis and purification of HPYD are shown in FIG. 1A.

The TFA agent used in the experimental scheme in FIG. 1A is TFA:$CH_2Cl_2$ (v/v)=2:98.

Figure 1B:
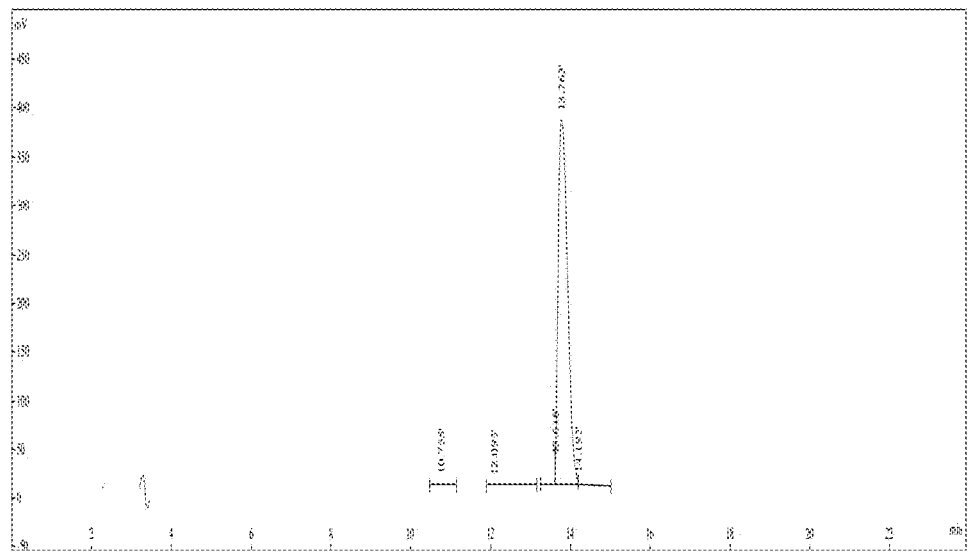
FIG. 1B shows the result of chromatographic analysis of HPYD.

The crude peptide product prepared was purified by HPLC, producing the final peptide with a purity>95%. The results of HPLC are shown in FIG. 1B.

Figure 1C:
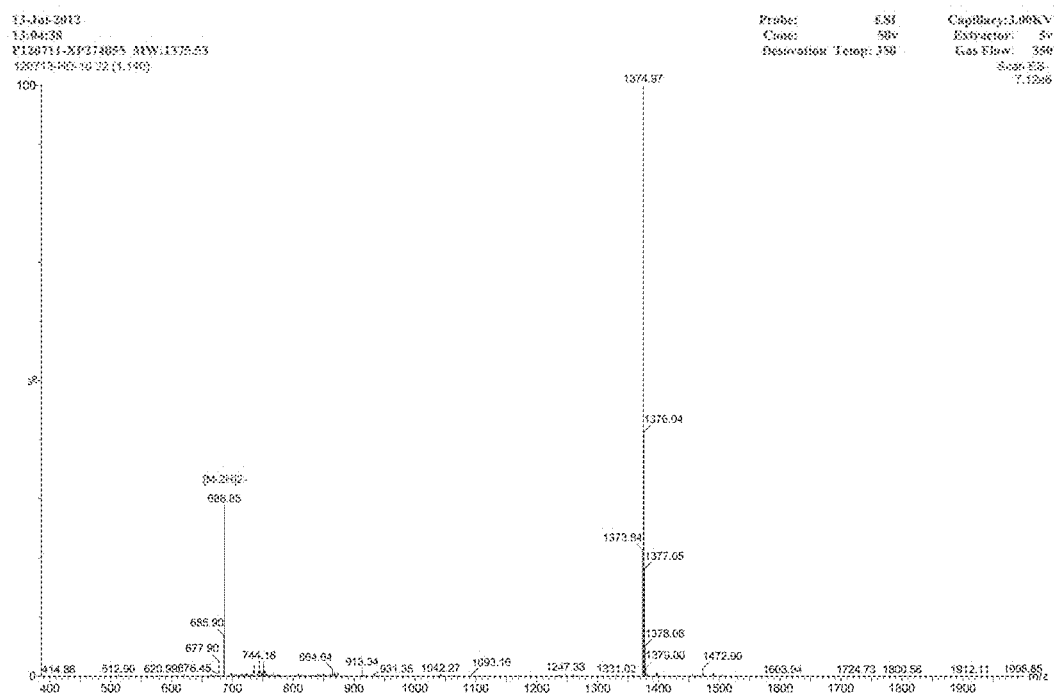
FIG. 1C shows the result of mass spectrometric detection for HPYD.

The polypeptide HPYD prepared and purified by the above-mentioned method was identified by mass spectrometry analysis and sequenced. The results of mass spectrometry analysis are shown in FIG. 1C. The results of identification and sequencing showed that the polypeptide prepared by the above method has the expected sequence and molecular weight.

Example 2. The Inhibition Effect of HPYD on $A\beta_{1-42}$ Aggregation and Fiber Formation 1. Materials and Methods
1.1 Drugs and Reagents $A\beta_{1-42}$ (purity>95%), Thioflavin T (ThT), PBS buffering powder were all purchased from Sigma, Inc. (US). β-sheet blocking peptides H102 and HPYD were synthesized by the method described in Example 1 and purified by High Performance Liquid Chromatography (HPLC). They were both identified by mass spectrum (MS) analysis with a purity>95%.

1.2 the Inhibition Effect of HPYD on Aβ Aggregation was Analyzed by ThT Fluorescence Spectrophotometry.

The degree of Aβ aggregation may be reflected by ThT fluorescence intensity. $A\beta_{1-42}$ lyophilized powder was formulated in 50 mmol/L PBS phosphate buffer (pH 7.4) to obtain a solution in a concentration of 22.15 μmol/L. The polypeptides H102 and HPYD were also formulated in 50 mmol/L PBS phosphate buffer (pH 7.4) to obtain a solution in a concentration of 88.60 μmol/L. In the experiment, $A\beta_{1-42}$ was mixed with H102 or HPYD in 1:1 volume ratio to a final concentration of 11.07 μmol/L and 44.3 μmol/L, respectively. The above two solutions were incubated at 37° C. for 24 h, and 10 μl of each solution was taken out and quickly mixed with 990 μl of 3.0 μmol/L ThT PBS. ThT fluorescence intensity was measured by using VARIAN PTC-Au00-01058 fluorescence spectrophotometer at the excitation wavelength of 453 nm and emission wavelength of 478-486 nm.

1.3 the Inhibition Effect of HPYD on $A\beta_{1-42}$ Aggregation was Observed by FT-IR Spectrometry.

22.15 μmol/L $A\beta_{1-42}$ solution in PBS phosphate buffer was formulated in quadruplicate as described in the above 1.2 section. To two solutions, PBS phosphate buffer was added in equal volume respectively and incubated alone at 37° C. for 30 min (30 min, aging group) and 72 h (72 h, aging group). To the other two solutions, H102 (88.60 μmol/L) and HPYD (88.60 μmol/L) were added in equal volume respectively and co-incubated at 37° C. for 72 h. After incubation, each sample was vacuum lyophilized. Then, 3.5 μg of H102 and 3.7 μg of HPYD were respectively mixed with anhydrous potassium bromide (120-180 mg) thoroughly, and pressurized for 5 min by tablet machine to form potassium bromide tablet. The measurement and analysis were carried out by using Nicolet Magna 760 FT-IR instrument, with a resolution of 4 $cm^{-1}$ and a spectrum range of 3500-400 $cm^{-1}$. The amide I band spectrum at 1700-1600 $cm^{-1}$ was analyzed using Origin 8.0 software. The fitting range was expanded to 1750-1550 $cm^{-1}$ due to the complexity of the components in the samples and the effect of vibration peaks close to amide I band on the secondary structure.

1.4 the Inhibition Effect of HPYD on Aβ Aggregation was Observed by Using Electron Microscope.

Aβ$_{1-42}$ solution in PBS phosphate buffer (11.07 μmol/L, 20 μl) was formulated as described in the above 1.2 section, and incubated alone at 37° C. for 5 days. Meanwhile, Aβ$_{1-42}$ (22.15 μmol/L, 10 μl) was respectively co-incubated with H102 or HPYD (88.61 μmol/L, 10 μl) under the same conditions for 5 days. 5 μl sample was taken from each group and dropped on the carbon support film on 300-mesh deionized copper grids, and then kept still at ambient temperature for 15 min. The samples were negatively stained in dark with 2% uranyl acetate for 2 min. After drying, the samples were observed using transmission electron microscope.

In the above-mentioned studies, Aβ$_{1-42}$ was used as negative control, and H102 was used as positive control.

2. Experiment Results 2.1 the Effect of Drugs on Aβ$_{1-42}$ Aggregation and Fiber Formation was Analyzed by ThT Fluorescence.

Aβ$_{1-42}$ in PBS solution could produce an extremely high fluorescence intensity, indicating that Aβ$_{1-42}$ can self-aggregate and form Aβ fibers. The fluorescence intensity from the aging group (in which Aβ$_{1-42}$ lyophilized powder was formulated in 50 mmol/L PBS phosphate buffer (pH 7.4) to obtain a solution in a concentration of 11.07 μmol/L, and the obtained solution was incubated at 37° C. for 24 hours) from which baseline fluorescence intensity was subtracted would be taken as 100%, and the inhibitory rate of the drug on Aβ$_{1-42}$ in each group was calculated. The results shown in Table 1 indicate that the inhibitory rate of HPYD on Aβ$_{1-42}$ is higher than that of H102.

TABLE 1

The inhibition effect of HPYD on Aβ$_{1-42}$ aggregation ($\bar{x} \pm S$, %)

| Sample ID | Inhibitory rate (%) |
| --- | --- |
| Aβ$_{1-42}$ | 0.00 ± 0.00 |
| H102 | 14.168 ± 0.038* |
| HPYD | 27.013 ± 0.018* |

Compared with Aβ$_{1-42}$ group, by F test:
*$P < 0.05$

Inhibitory rate=(the relative fluorescence intensity of 1-β sheet blocking peptide/the relative fluorescence intensity of Aβ$_{1-42}$)×100%

2.2 the Inhibition Effect of HPYD on Aβ$_{1-42}$ Aggregation was Observed by FT-IR Spectrometry.

Figure 2:
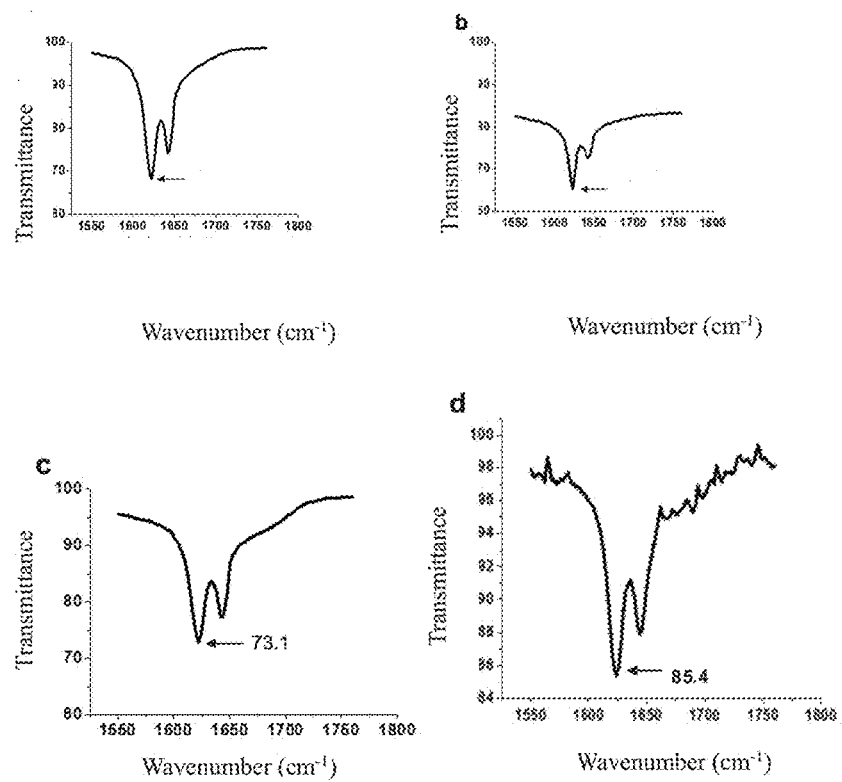
FIG. 2 shows Aβ aging group and the FT-IR spectrum thereof after HPYD intervention, wherein a is the FT-IR spectrum after incubation of Aβ solution for 30 minutes; b is the FT-IR spectrum after incubation of Aβ solution for 72 hours; c is the FT-IR spectrum after co-incubation of H102 and Aβ solution for 72 hours; and d is the FT-IR spectrum after co-incubation of HPYD and Aβ solution for 72 hours.

The secondary structures of Aβ$_{1-42}$ mainly include random coil, α-helix, β-sheet (extended structure) and β-turn. As shown in FIG. 2, in the wavenumbers representing β-sheet (1640-1620 cm$^{-1}$), the maximum negative peaks in the curves for each group are all in proximity to 1624 cm$^{-1}$, wherein the transmittance of HPYD group is significantly higher than that of the aging group (especially, the transmittance of 72 h aging group is the lowest). The content of β-sheet in HPYD group is the lowest. The content of β-sheet increases over the incubation time. HPYD group and H102 group have significantly higher transmittance in each wavenumber representing their secondary structures than the group in which Aβ was incubated alone for 72 h.

2.3 the Inhibition of HPYD on Aβ Aggregation was Observed Using Electron Microscope.

Figure 3:
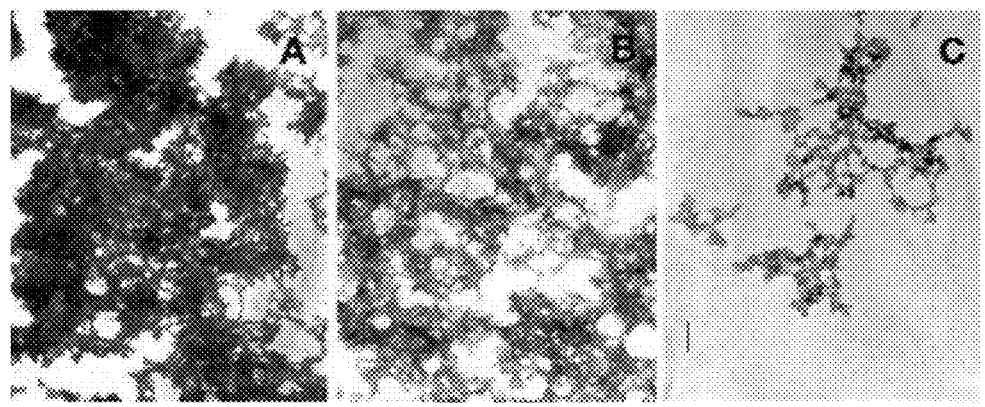
FIG. 3 shows the electron microscopy results of the inhibition of Aβ aggregation by HPYD.

The inhibition of HPYD on Aβ aggregation was observed using electron microscope, as shown in FIG. 3. A: When Aβ$_{1-42}$ was incubated alone for 5 days, a large number of Aβ fibers appeared. These fibers aggregated in a prick-type crystallization, with branches and largely woven into dark stained, dense networks, interspersed with a small amount of amorphous structures in an aggregation state; B: When H102 and Aβ$_{1-42}$ were co-incubated for 5 days, Aβ fibers were significantly decreased. They aggregated in a prick-type crystallization, with branches and woven into networks, interspersed with amorphous structures in an aggregation state; C: When HPYD and Aβ$_{1-42}$ were co-incubated for 5 days, the formed of Aβ fibers were significantly decreased and thinner, woven into light stained networks, interspersed with a minimal amount of amorphous structures in an aggregation state. The results of electron microscopy shown that HPYD has a stronger inhibition effect on Aβ aggregation than H102.

Conclusion

HPYD could inhibit Aβ aggregation and fiber formation.

Example 3. The Effect of HPYD on the Expressions of Aβ and APP in the Brains of APP/PS1 Double Transgenic Mice 1. Materials and Methods 1.1 Animals: Fourteen APP/PS1 double transgenic mice were randomized into model group and drug administration group. Seven C57BL/6J mice with the same age and genetic background were used in normal control group. These mice were all purchased from the Experimental Animal Research Center of Peking Union Medical College, Chinese Academy of Medical Sciences. By way of nasal administration, 33 mg/ml HPYD in physiological saline solutions were administered to the mice in drug administration group at a rate of 5 μl/d using drug delivery devices, and the same volume of physiological saline solutions were administered nasally to the mice in normal control group and model group. The detection was carried out 30 days after the administration.

1.2 Drugs and reagents: Anti-Aβ$_{1-42}$ antibody was purchased from Chemicon Inc. Anti-APP antibody, ready-to-use SABC Immunohistochemistry Staining Kit, DBA Color Development Kit and 0.1% polylysine were purchased from Wuhan Boster Biological Technology, Ltd. Other reagents have analytical purity.

1.3 Immunohistochemical Staining: After Morris Water Maze was carried out in order to determine the learning ability of the experimental mice, the mice were anaesthetized by celiac injection with 0.1 kg/L chloral hydrate at a dose of 4 ml/kg. Rapid intubation was carried out via left ventricle. In the meantime, the right atrium was incised, and 0.01 M PBS buffer was rapidly infused. When the liver became white, the brain was rapidly removed on ice bath and put into a 4% paraformaldehyde solution, fixed for more than 24 h. After the brain tissue sank, it was embedded in paraffin. The brain of the mouse was sliced along the sagittal section. When the hippocampus CA1 area was exposed, it was continuously sliced, with a thickness of 5 μm. Immunohistochemical staining: (1) The tissue slices were conventionally dewaxed; (2) The slices were incubated with 3% H$_2$O$_2$ at room temperature for 10 min to eliminate the activity of endogenous enzymes. (3) The slices were put into the citrate buffer and boiled in a microwave for antigen retrieval. The procedure was carried out for twice, each for 5 min (5 min×2 times). Then the slices were taken out and cooled to room temperature. (4) Diluted primary antibodies Aβ (1:100) and APP (1:100) were respectively added to the tissue slices in an amount sufficient to cover the tissues. The tissues were kept at 4° C. in a refrigerator overnight. (5) According to the sources of the primary antibodies, the corresponding biotin-labeled Goat-anti-Mouse and Goat-anti-Rabbit universal secondary antibodies were respectively added dropwise in an amount sufficient to cover the tissues. The tissues were incubated at 37° C. for 20 min. (6) SABC solutions were added dropwise in an amount sufficient to cover the tissues. The tissues were incubated at 37° C. for 20 min. (7) Color development was carried out using DAB chromogenic agent. The degree of staining was controlled under the microscope. Deionized water was used to terminate the color development. The tissue slices were washed thoroughly. (8) The tissue slices were dehydrated with ethanol gradients, transparentized with xylene, sealed with neutral gums, and observed under microscope. For the negative control, the steps are identical expect that 0.01 M PBS solution was used to replace primary antibody.

1.4 Data processing: The obtained data is expressed in mean±standard deviation ($\bar{\chi} \pm S$). Statistical analysis was performed using statistical software SPSS16.0. P<0.05 represents that the difference is statistically significant.

2. Results 2.1 Immunohistochemical Staining of Aβ

Figure 4:
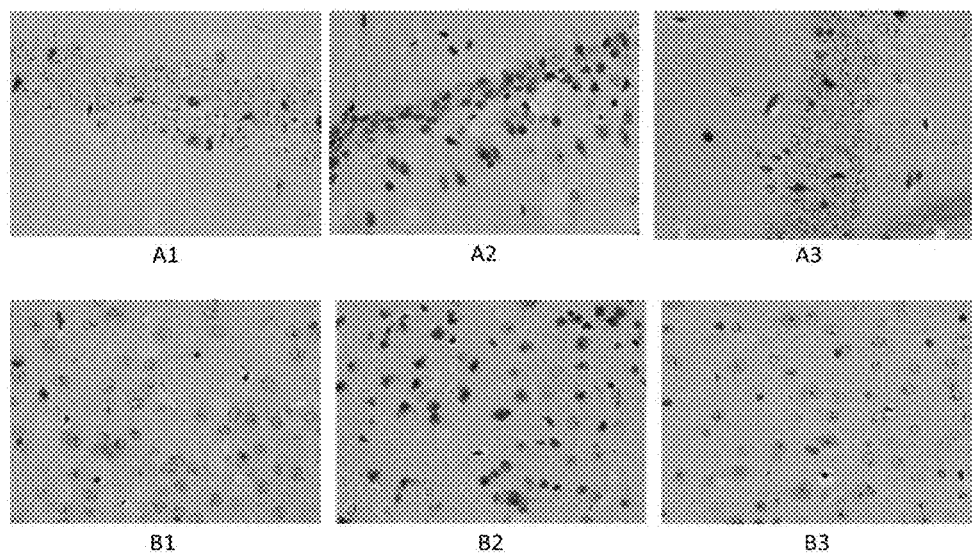
FIG. 4 shows the effects of HPYD on Aβ expression in the cerebral cortex and hippocampus CA1 region of APP/PSI double transgenic mice, wherein A1 shows Aβ expression in the hippocampus CA1 region of normal control group; A2 shows Aβ expression in the hippocampus CA1 region of model group; A3 shows Aβ expression in the hippocampus CA1 region of drug administration group; B1 shows A β expression in the cerebral cortex of normal control group; B2 shows Aβ expression in the cerebral cortex of model group; B3 shows Aβ expression in the cerebral cortex of drug administration group.

The results of immunohistochemical staining of Aβ show that, in normal control group, the cytoplasm coloring of neurons in hippocampus CA1 area and cortex is negative or weakly positive, and the ratio of positive cells (the number of positive cells/the number of total cells) is low. Compared with normal control group, model group has more positive cells and increased ratio of positive cells. The difference is statistically significant (P<0.01). In the model group, the cytoplasm coloring is significantly deeper, and Aβ expression is enhanced. Compared with model group, drug administration group has lighter cytoplasm coloring and decreased ratio of positive cells. The difference is statistically significant (P<0.01). In drug administration group, Aβ expression is weaker, and there is no significant difference between drug administration group and normal control group (P>0.05). See Table 2 and FIG. 4.

TABLE 2

Comparison of Aβ activity in cortex and hippocampus CA1 area among three mouse groups (n = 7, $\bar{x} \pm S$)

| group | ratio of positive cells (%) | |
| --- | --- | --- |
| | Cortex | Hippocampus CA1 area |
| Normal control group | 16.56 ± 3.49 | 10.82 ± 2.21 |
| Model group | 79.40 ± 6.54## | 54.27 ± 5.53## |
| Drug administration group | 15.85 ± 2.77** | 11.09 ± 2.47** |

Compared with normal control group,
P < 0.01;
compared with model group,
**P < 0.01

2.2 Immunohistochemical Staining of APP

Figure 5:
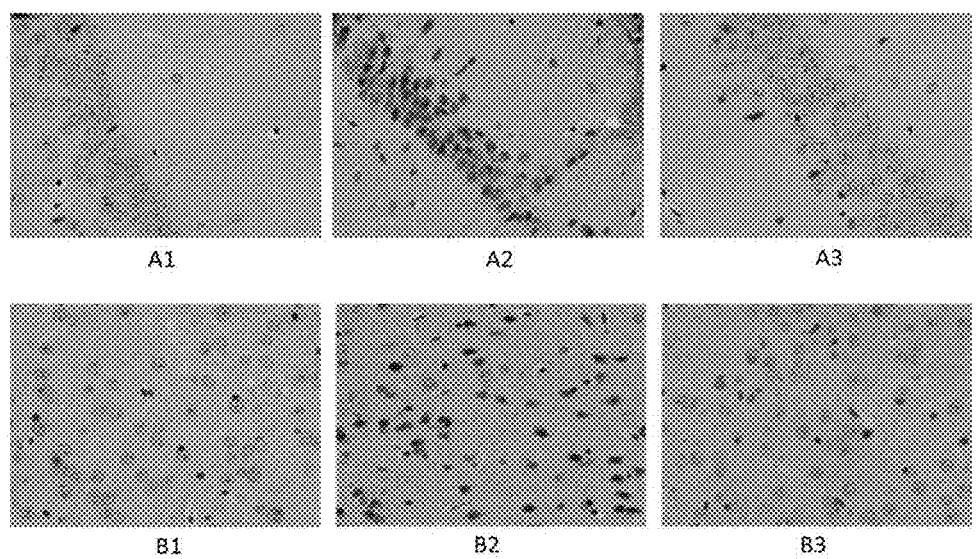
FIG. 5 shows the effects of HPYD on APP expression in the cerebral cortex and hippocampus CA1 region of APP/PSI double transgenic mice, wherein A1 shows APP expression in the hippocampus CA1 region of normal control group; A2 shows APP expression in the hippocampus CA1 region of model group; A3 shows APP expression in the hippocampus CA1 region of drug administration group; B1 shows APP expression in the cerebral cortex of normal control group; B2 shows APP expression in the cerebral cortex of model group; B3 shows APP expression in the cerebral cortex of drug administration group.

The results of immunohistochemical staining of APP show that, in normal control group, the cytoplasm coloring of neurons in hippocampus CA1 area and cortex is negative or weakly positive, and the ratio of positive cells is low. Compared with normal control group, model group has more positive cells and increased ratio of positive cells. The difference is statistically significant (P<0.01). In the model group, the cytoplasm coloring is significantly deeper, and APP expression is enhanced. Compared with model group, drug administration group has lighter cytoplasm coloring and decreased ratio of positive cells. The difference is statistically significant (P<0.01). In drug administration group, APP expression is weaker, and there is no significant difference between drug administration group and normal control group (P>0.05). See Table 3 and FIG. 5.

TABLE 3

Comparison of APP activity in cortex and hippocampus CA1 area among three mouse groups (n = 7, $\bar{x} \pm S$)

| group | ratio of positive cells (%) | |
| --- | --- | --- |
| | Cortex | Hippocampus CA1 area |
| Normal control group | 13.68 ± 1.49 | 11.80 ± 3.68 |
| Model group | 82.45 ± 9.98## | 49.12 ± 11.33## |
| Drug administration group | 14.25 ± 3.25** | 12.75 ± 1.83** |

Compared with normal control group,
P < 0.01;
compared with model group,
**P < 0.01

3. Conclusion

After HPYD is administered nasally and delivered into the brain, it can reduce the expressions of APP and Aβ proteins in the brain.

Example 4. The Effect of HPYD on the Behaviors of APP/PS1 Double-Transgenic Mice 1. Materials and Methods 1.1 Animals: Fourteen APP/PS1 double transgenic mice were randomized into model group and drug administration group. Seven C57BL/6J mice with the same age and genetic background were used in normal control group. By way of nasal administration, 33 mg/ml HPYD in physiological saline solutions were administered to the mice in drug administration group in a rate of 5 μl/d using drug delivery devices, and the same volume of physiological saline solutions were administered nasally to the mice in normal control group and model group. The detection was performed 30 days after the administration.

1.2 Morris Water Maze test: (1) Place Navigation: A platform is placed in a circle within the third quadrant of water maze. Each mouse swims twice (90 s/time) during the same time periods of every day for 5 days. The time required for a mouse's finding and climbing onto the platform, i.e. escape latency, is recorded. If the mouse could not find the platform within 90 s, it is guided to the platform and kept for 20 s. In this case, the escape latency is recorded as 90 s. (2) Spatial Probe: The platform is removed at day 6, and during the same time period, a water entry point is optionally selected for putting a mouse into water. Each mouse swims once (90 s/time). The swim track of the mouse within 90 s, the numbers of leaping over the hidden platform, the original swimming angle after water entry, and so on are recorded for testing the memory ability of the mouse.

1.3 Data processing: The data obtained is expressed in mean±standard deviation ($\bar{\chi} \pm S$). Statistical analysis was performed using statistical software SPSS16.0. One-way ANOVA and pairwise comparison were employed. P<0.05 represents that the difference is statistically significant.

2. Results 2.1 Results of Place Navigation Test

Figure 6:
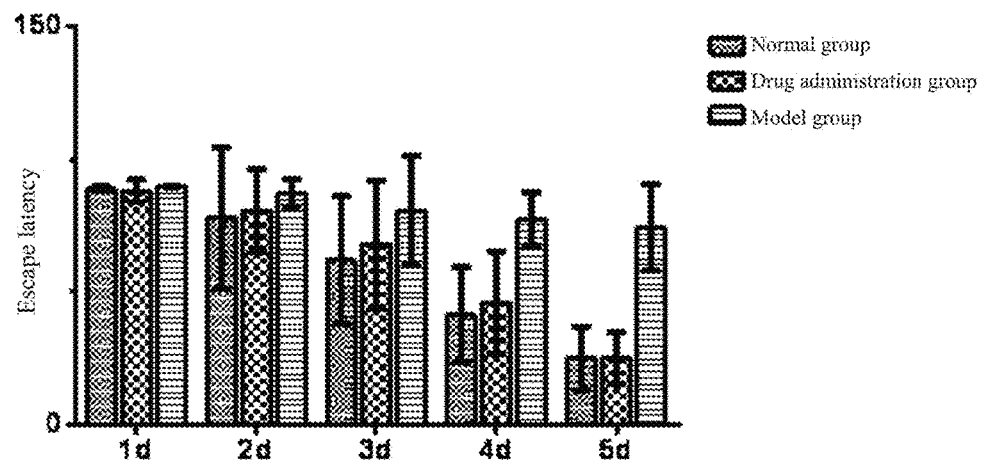
FIG. 6 shows the daily mean escape latency of mice in each mouse group in place navigation test.

Compared with the mice in normal control group, the mice in model group have significantly longer escape latency. The difference between the two groups is statistically significant (P<0.01). Compared with the mice in model group, the mice in drug administration group have decreased escape latency. The difference between the two groups is statistically significant (P<0.01). For drug administration group and control group, the escape latency is generally decreased with the experiment numbers increase. The difference between the two groups is not statistically significant (P>0.05). See Table 4 and FIG. 6.

TABLE 4

Variations of daily mean escape latency of mice in each group (s, n = 7, x̄ ± S)

| Time | Control group | Model group | Drug administration group |
|------|---------------|-------------|---------------------------|
| 1 d  | 88.992 ± 0.845 | 89.809 ± 0.064## | 88.127 ± 4.137** |
| 2 d  | 77.785 ± 26.687 | 87.230 ± 5.249## | 80.404 ± 15.646** |
| 3 d  | 62.062 ± 24.064 | 80.431 ± 20.821## | 67.740 ± 24.389** |
| 4 d  | 41.281 ± 17.749 | 77.422 ± 10.138## | 45.950 ± 19.211** |
| 5 d  | 25.094 ± 11.932 | 74.100 ± 16.320## | 24.974 ± 9.685** |

Compared with normal control group
P < 0.01;
compared with model group,
**P < 0.01

2.2 Results of Spatial Probe Test

Figure 7:
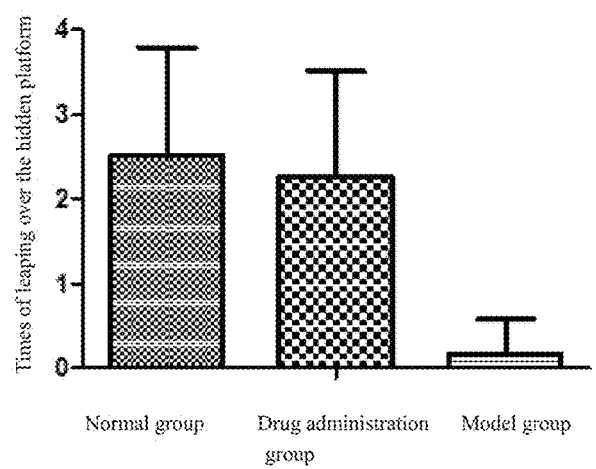
FIG. 7 shows the comparison result of the numbers of leaping over the hidden platform in each mouse group in spatial probe test.
Figure 8:
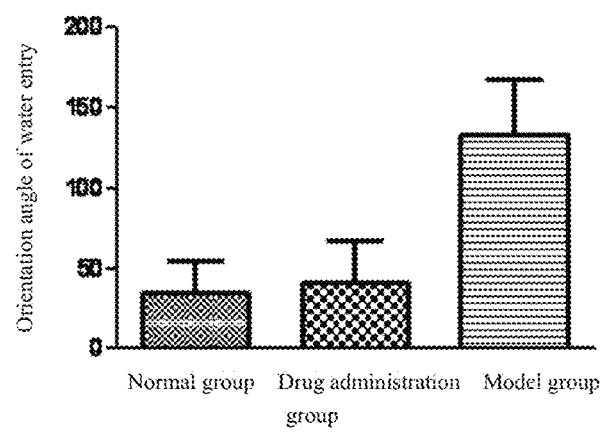
FIG. 8 shows the comparison result of the orientation angles of water entry in each mouse group in spatial probe test.

The numbers of leaping over the hidden platform and orientation angles of mice in three groups are compared. Compared with the mice in normal control group, the mice in model group have significantly decreased numbers of leaping over the hidden platform and significantly increased orientation angles (the angle between the swimming orientation upon water entry and the line linking entry point and the platform). The difference between the two groups is statistically significant (P<0.01). Compared with the mice in model group, the mice in drug administration group have increased numbers of leaping over the hidden platform, and decreased orientation angles. The difference between the two groups is statistically significant (P<0.01). The difference between drug administration group and normal control group is not statistically significant (P>0.05). See Table 5 and FIGS. 7 and 8.

TABLE 5

Comparison of numbers of leaping over the hidden platform and original angles of mice in three groups in spatial probe test (n = 7, x̄ ± S)

| Group | numbers of leaping over the hidden platform (numbers) | Orientation angles (degree) |
|-------|-------------------------------------------------------|------------------------------|
| Control group | 2.50 ± 1.291 | 34.124 ± 20.192 |
| Model group | 0.16 ± 0.304## | 156.072 ± 17.941## |
| Drug administration group | 2.25 ± 1.258** | 40.478 ± 26.533** |

Compared with normal control group,
P < 0.01;
Compared with model group
**P < 0.01

Conclusion

After HPYD is administered nasally and delivered to the brain via olfactory route, it can significantly improve the learning ability of AD model mice.

In the present application, various publications are cited, which are incorporated herein by reference in their entirety, in order to describe the state of the art to which the invention pertains in more detail.

It is apparent to those skilled in the art that various modifications and alterations can be made to the invention without departing the scope and spirit thereof. Other embodiments of the invention are obvious for those skilled in the art by considering the description and examples disclosed herein. The description and examples are intended to be interpreted as only exemplary, and the actual scope and spirit of the invention are defined in the attached claims.

The invention claimed is:

1. A polypeptide comprising the following amino acid sequence:

(SEQ ID NO: 1)
His-Lys-Gln-Leu-Pro-Phe-Tyr-Glu-Glu-Asp.

2. The polypeptide according to claim 1, the polypeptide consisting of the following amino acid sequence:

(SEQ ID NO: 1)
His-Lys-Gln-Leu-Pro-Phe-Tyr-Glu-Glu-Asp.

3. A pharmaceutical composition comprising the polypeptide according to claim 1 and a pharmaceutically acceptable carrier.

4. A pharmaceutical composition comprising the polypeptide according to claim 2 and a pharmaceutically acceptable carrier.

5. A method for treating Alzheimer's disease in a subject, comprising administering an effective amount of the polypeptide according to claim 1 to the subject.

6. A method for treating Alzheimer's disease in a subject, comprising administering an effective amount of the polypeptide according to claim 2 to the subject.

\* \* \* \* \*

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: Peptide

<400> SEQUENCE: 1

His Lys Gln Leu Pro Phe Tyr Glu Glu Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Peptide

<400> SEQUENCE: 2

His Lys Gln Leu Pro Phe Phe Glu Glu Asp
1               5                   10

<210> SEQ ID NO 3
<211> LENGTH: 42
```

```
<212> TYPE: PRT
<213> ORGANISM: Artificial Sequence
<220> FEATURE:
<223> OTHER INFORMATION: Peptide

<400> SEQUENCE: 3

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```